United States Patent
Amthor et al.

(10) Patent No.: US 10,321,845 B2
(45) Date of Patent: Jun. 18, 2019

(54) MAGNETIC RESONANCE FINGERPRINTING IN SLICES ALONG A ONE-DIMENSIONAL EXTENSION

(71) Applicant: KONINKLIJKE PHILIPS N.V., Eindhoven (NL)

(72) Inventors: Thomas Erik Amthor, Eindhoven (NL); Mariya Ivanova Doneva, Eindhoven (NL); Peter Koken, Eindhoven (NL); Jochen Keupp, Eindhoven (NL); Peter Boernert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 110 days.

(21) Appl. No.: 15/525,145

(22) PCT Filed: Oct. 30, 2015

(86) PCT No.: PCT/EP2015/075194
§ 371 (c)(1),
(2) Date: May 8, 2017

(87) PCT Pub. No.: WO2016/074946
PCT Pub. Date: May 19, 2016

(65) Prior Publication Data
US 2017/0319097 A1    Nov. 9, 2017

(30) Foreign Application Priority Data
Nov. 14, 2014  (EP) .................................... 14193155

(51) Int. Cl.
*G01V 3/00*     (2006.01)
*A61B 5/055*    (2006.01)
(Continued)

(52) U.S. Cl.
CPC ............ *A61B 5/055* (2013.01); *A61B 5/4872* (2013.01); *G01R 33/307* (2013.01);
(Continued)

(58) Field of Classification Search
CPC .... G01R 33/4828; G01R 33/50; G01R 33/54; G01R 33/445; G01R 33/543;
(Continued)

(56) References Cited

U.S. PATENT DOCUMENTS

2013/0265047 A1   10/2013   Griwold et al.
2013/0271132 A1   10/2013   Griswold
(Continued)

OTHER PUBLICATIONS

Ma et. al., "Magnetic Resonance Fingerprinting," Nature, vol. 495, pp. 187 to 193, doi:10.1038/nature11971.
(Continued)

*Primary Examiner* — Rodney E Fuller

(57) ABSTRACT

The invention provides for a magnetic resonance imaging system (100) which comprise a magnet (104) and a magnetic field gradient generator (110, 112) for generating a gradient magnetic field within an imaging zone (108). The gradient magnetic field is aligned with a predetermined direction. The magnetic resonance imaging system further comprise a memory (134, 136) for storing machine executable instructions (150, 152, 154), a pre-calculated magnetic resonance fingerprinting dictionary (144), and pulse sequence instructions (140). The pulse sequence instructions cause the magnetic resonance imaging system to acquire the magnetic resonance data according to a magnetic resonance fingerprinting technique. The magnetic resonance fingerprinting technique encodes the magnetic resonance data as slices (125). The pre-calculated magnetic resonance fingerprinting dictionary contains a listing of calculated magnetic resonance signals in response to execution of the pulse sequence instructions for a set of predetermined substances. Execution
(Continued)

of the machine executable instructions causes a processor (130) controlling the magnetic resonance imaging system to: acquire (300) the magnetic resonance data by controlling the magnetic resonance imaging system with pulse sequence instructions; divide (302) the magnetic resonance data into a set of slices; calculate (304) the abundance of each of the set of predetermined substances within each of the set of slices by comparing the magnetic resonance data for each of the set of slices with the pre-calculated magnetic resonance fingerprinting dictionary; and calculate (306) a magnetic resonance fingerprint chart by plotting abundance of each of the set of predetermined substances within each of the set of slices as a function of position along the predetermined direction.

14 Claims, 4 Drawing Sheets

(51) Int. Cl.
| | |
|---|---|
| *G01R 33/30* | (2006.01) |
| *G01R 33/48* | (2006.01) |
| *G01R 33/483* | (2006.01) |
| *G01R 33/50* | (2006.01) |
| *G01R 33/54* | (2006.01) |
| *A61B 5/00* | (2006.01) |
| *G01R 33/563* | (2006.01) |

(52) U.S. Cl.
CPC ..... *G01R 33/4828* (2013.01); *G01R 33/4835* (2013.01); *G01R 33/50* (2013.01); *G01R 33/54* (2013.01); *G01R 33/563* (2013.01)

(58) Field of Classification Search
CPC .............. G01R 33/4625; G01R 33/546; G01R 33/56563; G01R 33/4835; G01R 33/243; G01R 33/465; G01R 33/4804; G01R 33/482; G01R 33/4822; G01R 33/4824; G01R 33/4826; G01R 33/56; G01R 33/5601; G01R 33/5611; G01R 33/5612; G01R 33/5615; G01R 33/5616; G01R 33/5617
USPC ....................................................... 324/309
See application file for complete search history.

(56) References Cited

U.S. PATENT DOCUMENTS

| | | | | |
|---|---|---|---|---|
| 2017/0003365 | A1* | 1/2017 | Rosen | G01R 33/445 |
| 2017/0299683 | A1* | 10/2017 | Cohen | G01R 33/56366 |
| 2017/0315193 | A1* | 11/2017 | Amthor | A61B 5/055 |
| 2018/0031653 | A1* | 2/2018 | Boernert | G01R 33/4625 |
| 2018/0106876 | A1* | 4/2018 | Nielsen | G01R 33/4828 |
| 2018/0238983 | A1* | 8/2018 | Cohen | G01R 33/543 |
| 2018/0292486 | A1* | 10/2018 | Gulani | G01R 33/4835 |

OTHER PUBLICATIONS

Mat et al Using Gradient Waveforms Derived from Music in MR Fingerprinting to Increase Patient Comfort Proc. Intl. Soc. Mag. Reson. Med. 22 (2014).

Cohen et al "Magnetic Resonance Fingerprinting Trajectory Optimization" Proc. Intl. Soc. Mag. Reson. Med. 22 (2014).

Jiang et al "Simultaneous T1, T2, Diffusion and Proton Density Quantification with MR Fingerprinting" Proc. Intl. Soc. Mag. Reson. Med. 22 (2014).

Deshmane et al "Validation of Tissue Characterization in Mixed Voxels Using MR Fingerprinting" Proc. Intl. Soc. Mag. Reson. Med. 22 (2014).

Madore et al "Quantitative MR imaging method" Proc. Intl. Soc. Mag. Reson. Med. 22 (2014).

Wright et al "Theoretical Framework for MR Fingerprinting with ASL: Simultaneous Quantification of CBF, Transit Time, and T1" Proc. Intl. Soc. Mag. Reson. Med. 22 (2014).

Lemasson et al "Vascular Fingerprinting in Rat Brain Tumors" Proc. Intl. Soc. Mag. Reson. Med. 22 (2014).

Wong et al "Optimization of Flip angle and TR schedules for MR Fingerprinting" Proc. Intl. Soc. Mag. Reson. Med. 22 (2014).

Geshnizjani et al A Serial Artificial Neural Network Model for TrueFISP Sequence Design Proc. Intl. Soc. Mag. Reson. Med. 22 (2014).

Chiu S-C et al: "MR Fingerprinting:Fat-Water separation imaging",Proceedings of the International Society for Magnetic Resonance in Medicine, 22nd Annual Meeting and Exhibition, Milan, Italy, May 10-16, 2014, vol. 22, No. 1668, Apr. 28, 2014.

Sakaie "Feasibility of Diffusion Tensor Imaging with Magnetic Resonance Fingerprinting" Proc. Intl. Soc. Mag. Reson. Med. 22 (2014).

Badve et al "Tissue characterization of Gliomas: Initial clinical experience with Magnetic Resonance Fingerprinting (MRF)" Proc. Intl. Soc. Mag. Reson. Med. 22 (2014) 3234.

Kansagra et al "Accelerated post-processing of MR fingerprinting data using partial signal library construction" Proc. Intl. Soc. Mag. Reson. Med. 22 (2014) 4223.

Jang et al "Iterative Compressed Sensing Reconstruction Using Forward Model Based on MR Multi-Parameter" Proc. Intl. Soc. Mag. Reson. Med. 22 (2014) 4283.

Cohen et al "15T Ultrahigh Field Fast MR Fingerprinting with Optimized Trajectories" Proc. Intl. Soc. Mag. Reson. Med. 22 (2014) 4285.

Eo et al "Effective data sharing method for extreme cartesian undersampling in MRF" Proc. Intl. Soc. Mag. Reson. Med. 22 (2014) 4286.

McGivney et al "Singular Value Decomposition for Magnetic Resonance Fingerprinting in the Time Domain" Proc. Intl. Soc. Mag. Reson. Med. 22 (2014) 4287.

Sarracanie et al "High Speed MR Fingerprinting at 6.5 mT" Proc. Intl. Soc. Mag. Reson. Med. 22 (2014) 4289.

Jiang et al "MR Fingerprinting Using FISP" Proc. Intl. Soc. Mag. Reson. Med. 22 (2014) 4290.

Wu et al "Motion Sensitivity in MR Fingerprinting" Proc. Intl. Soc. Mag. Reson. Med. 22 (2014) 4291.

Börnert et al:"Principles of Whole-Body Continuously-Moving-Table MRI", Journal of Magnetic Resonance Imaging. Society for Magnetic Resonance Imaging, Oak Brook, IL, US, vol. 28, Jun. 25, 2008 (Jun. 25, 2008), pp. 1-12.

Lu Ma et al: "Dosimetric evaluation for exposure of patient to a z-gradient coil in magnetic resonance imaging". Journal of Applied Physics, American Institute of Physics, US,vol. 109, No. 7,Mar. 18, 2011 (Mar. 18, 2011), pp. 7B301-7B3O1.

S.S. Hidalgo-Tobon: "Theory of gradient coil design methods for magnetic resonance imaging".Concepts in Magnetic Resonance Part A,vol. 36A,No. 4,Jul. 21, 2010 (Jul. 21, 2010),pp. 223-242.

Deka K et al: "Quantitative density profiling with pure phase encoding and a dedicated 1D gradient".Journal of Magnetic Resonance, Academic Press, Orlando, FL, US, vol. 178, No. 1,Jan. 1, 2006 (Jan. 1, 2006), pp. 25-32.

\* cited by examiner

MAGNETIC RESONANCE FINGERPRINTING IN SLICES ALONG A ONE-DIMENSIONAL EXTENSION

CROSS REFERENCE TO RELATED APPLICATIONS

This application is a U.S. national phase application of International Application No. PCT/EP2015/075194, filed on Oct. 30, 2015, which claims the benefit of EP Application Serial No. 14193155.0 filed on Nov. 14, 2014 and is incorporated herein by reference.

TECHNICAL FIELD

The invention relates to magnetic resonance imaging, in particular to magnetic resonance fingerprinting.

BACKGROUND OF THE INVENTION

Magnetic Resonance (MR) fingerprinting is a new technique where a number of RF pulses, distributed in time, are applied such that they cause signals from different materials or tissues to have a unique contribution to the measured MR signal. A limited dictionary of precalculated signal contributions from a set or fixed number of substances is compared to the measured MR signals and within a single voxel the composition can be determined. For example if it is known that a voxel only contains water, fat, and muscle tissue the contribution from these three materials need only be considered and only a few RF pulses are needed to accurately determine the composition of the voxel.

The magnetic resonance fingerprinting technique was introduced in the journal article Ma et. al., "Magnetic Resonance Fingerprinting," Nature, Vol. 495, pp. 187 to 193, doi:10.1038/nature11971. The magnetic fingerprinting technique is also described in United States patent applications US 2013/0271132 A1 and US 2013/0265047 A1.

SUMMARY OF THE INVENTION

The invention provides for a magnetic resonance imaging system, a method and a computer program product in the independent claims. Embodiments are given in the dependent claims.

The Nature article by Ma et. al. introduces the basic idea of magnetic resonance fingerprinting and terminology which is used to describe this technique such as the dictionary, which is referred to herein as a "pre-calculated magnetic resonance fingerprinting dictionary," a "magnetic resonance fingerprinting dictionary," and a "dictionary."

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a magnetic resonance imaging system for acquiring a magnetic resonance fingerprint chart from a subject within an imaging zone. A magnetic resonance fingerprint chart as used herein encompasses data or a rendering of data which describes or plots the concentrations of various substances as a function of distance along a one-dimensional extension or along an axis. The data for the magnetic resonance fingerprint chart is acquired using magnetic resonance fingerprinting. The magnetic resonance imaging system comprises a magnet for generating a main magnetic field within the imaging zone. The main magnetic field is sometimes referred to as the B0 field. The magnetic resonance imaging system further comprises a magnetic field gradient generator for generating a gradient magnetic field within the imaging zone. The gradient magnetic field is aligned with a predetermined direction.

The magnetic field generator may take several different forms. In one example the magnetic field gradient generator is a magnetic field gradient coil for generating the gradient magnetic field. In other instances the magnetic field gradient generator is a modification of the magnet itself. Since the magnet could be modified such that the main magnetic field has a permanent gradient magnetic field within it. The gradient magnetic field is aligned with a predetermined direction. The magnetic resonance fingerprint chart has its one-dimensional extension along the predetermined direction. The magnetic resonance imaging system further comprises a memory for storing machine-executable instructions, a pre-calculated magnetic resonance fingerprinting dictionary and pulse sequence instructions. The pulse sequence instructions are instructions or a timing information which can be converted into instructions which cause the magnetic resonance imaging system to acquire the magnetic resonance data according to a magnetic resonance fingerprinting technique. The magnetic resonance fingerprinting technique encodes the magnetic resonance data preferably as slices. The pre-calculated magnetic resonance fingerprinting dictionary contains a listing of calculated magnetic resonance signals as a potential MR signal response to the Fingerprinting sequence for a set of predetermined substances. The various predetermined substances different properties such as T1 or T2 times which cause them to generate a particular Magnetic Resonance signal.

Each pre-calculated magnetic resonance fingerprinting dictionary entry represents the response of a particular substance to the entire pulse sequence. The entries in the dictionary are the calculated magnetic resonance signal at specified measurement times to correspond to actual measurement times. The MR signals in the dictionary can be calculated by modeling the response of each of the substances using the well known Bloch equation to the pulse sequence. These predicted MR signal values can then be compared to the measured MR signals. Each of the substances in the dictionary can potentially make a positive contribution to the measured MR signal. A comparison at all or many measurement times enables an accurate deconvolution of the composition, in terms of the substances in the magnetic resonance fingerprinting dictionary, of the region contributing to the measured magnetic resonance signal.

The magnetic resonance imaging system further comprises a processor for controlling the magnetic resonance imaging system. Execution of the machine-executable instructions causes the processor to acquire the magnetic resonance data by controlling the magnetic resonance imaging system with the pulse sequence instructions. Execution of the machine-executable instructions further causes the processor to divide the magnetic resonance data into a set of slices. The slices may be located perpendicular to the predetermined direction. Execution of the machine-executable instructions further cause the processor to calculate the abundance of each of the predetermined substances within each of the set of slices by comparing the magnetic resonance data from each of the set of slices with the pre-calculated magnetic resonance fingerprinting dictionary.

Execution of the machine-executable instructions further cause the processor to calculate the abundance of each of the predetermined substances within each of the set of slices by comparing the magnetic resonance data for each of the set of slices with the pre-calculated magnetic resonance fingerprinting dictionary. Execution of the instructions further cause the processor to calculate the magnetic resonance fingerprint chart by plotting the abundance of each of the predetermined substances within each of the set of slices as a function of position along the predetermined direction.

The above magnetic resonance imaging system differs in at least that the magnetic resonance fingerprinting technique is performed along one dimension in the predetermined direction. Gradient fields for spatial encoding perpendicular to the predetermined direction are not used. This may lead to a number of benefits. One is that the magnetic resonance fingerprinting technique can be acquired extremely fast. Another advantage is that the magnetic resonance fingerprint chart can be used to locate the presence of small amounts of substances within the magnetic resonance fingerprinting dictionary. For example if a subject has cancer and a substance within the set of predetermined substances indicates cancer the subject can be very quickly scanned with the magnetic resonance imaging system and the substance which indicates the presence of cancer can be detected. This may then be used to trigger more detailed magnetic resonance fingerprinting in more than one dimension or even to trigger conventional magnetic resonance imaging to look at this region in detail. This technique is very sensitive to small amounts of a substance from a set of predetermined substances.

The set of slices may be determined by frequency bands in the magnetic resonance data.

The pulse sequence instructions may contain instructions to perform the measurement of the magnetic resonance data at varying repetition times, varying flip angles and varying measurement times per pulse repetition. This may provide a useful distribution of pulse times that provide a good sampling and allow matching of the different components to the magnetic resonance fingerprinting dictionary.

The sequence of RF pulses (flip angles), the repetition times etc, can be random or pseudorandom. In a pseudorandom sequence of RF pulses or in RF pulses selected from a distribution of possible RF pulses the sequence of the RF pulses may be chosen such that it maximize its encoding power to achieve the highest diversity between the potential MR responses for the different species. A main point is that the pulse sequence comprises a range of repetition times and flip angles instead of single values. This may be selected in a way that the resulting magnetic resonance signals are different for different tissues and resemble fingerprints.

The k-space sampling can be varied. For example uniform k-space sampling in one dimension, non-uniform k-space sampling in one dimension, and random k-space sampling in one dimension. When using a one dimensional slice selection, such as z-slice selection and sampling without x and y gradients (i.e., one whole z slice at a time), one might say that only a single point in k-space (the origin) is sampled. One could use the z gradient not for slice selection but for sampling k-space in z direction, again without x and y gradients. In this case, k-space would be one-dimensional and the sampling could be performed using a uniform or non-uniform distribution of points in k-space.

In another embodiment the pulse sequence comprises a train of pulse repetitions. Each pulse repetition of the train of the pulse repetitions has a random distribution, a preselected duration from distribution of durations, or a pseudorandom duration. The preselected duration may be selected from the distribution such that the resulting train of RF pulses appears to be random or pseudo-random, but may be chose to also optimize other properties. For example as already mentioned above, the RF pulses may be chosen such that they maximize the sequence's encoding power to achieve the highest diversity between the potential MR responses for the different species.

Each pulse repetition comprises a radio-frequency pulse chosen from a distribution of flip angles to rotate magnetic spins. These are magnetic spins of the subject within the imaging zone. Each pulse repetition comprises a sampling event where the magnetic resonance signal is sampled for a predetermined duration at a predetermined time before the end of the repetition time. The magnetic resonance data is acquired during the sample event.

The distribution of the flip angles for example could be a random distribution, a pseudorandom distribution, or a predetermined distribution which is chosen to give a good sampling. In magnetic resonance fingerprinting there needs to be a variety of different flip angles that are used hence the term distribution of flip angles is used.

In another embodiment each pulse repetition of the pulse sequence comprises a first 180° radio-frequency pulse performed at a first temporal midpoint between the radio-frequency pulse and a sampling event to re-focus the magnetic resonance signal. Each pulse repetition of the pulse sequence comprises a second 180° RF pulse performed at a second temporal midpoint between the sampling event and the start of the next pulse repetition. In this embodiment per pulse repetition there are two 180° radio-frequency pulses. These two 180° RF pulses re-focus the magnetic resonance signal. Their effect is that it eliminates or reduces the dependency of the signal on inhomogeneities in the B0 field. In magnetic resonance fingerprinting the data is highly dependent on how uniform the B0 field is. The magnetic resonance fingerprinting dictionary needs to take into account inhomogeneities in the B0 field for the calculations to be proper. By using the 180° RF re-focusing pulses this dependency on the inhomogeneity of the B0 field is reduced. This may enable the ability to more accurately calculate the abundance of each of the set of predetermined substances within each of the set of slices.

In particular, constructing the magnetic resonance fingerprinting dictionary is simplified. If the influence of B0 field variations on the signal are minimized and the measured signal is independent of dephasing effects then dictionary entries can be constructed by modeling a single spin with the Bloch equation. Without the use of the two 180° RF refocusing pulses the inhomogeneity of the B0 field needs to be taken into account when calculating dictionary entries. Using the 180° RF refocusing pulses therefore also improves the accuracy of the deconvolution when calculating the magnetic resonance fingerprint chart.

In another embodiment the calculation of the abundance of each of the predetermined tissue types within each of the set of slices by comparing the magnetic resonance data for each of the set of slices with the pre-calculated magnetic resonance fingerprinting dictionary is performed by expressing each magnetic resonance signal of the magnetic resonance data as a linear combination of the signal from each of the predetermined substances. This may be done such that there are no non-negative coefficients which are calculated. This is further accomplished by determining the abundance of each of the predetermined substances by solving the linear combination using a minimization technique. For example a modified least squares method could be used. The least squares method could be modified such that negative values of a particular substance are rejected.

In another embodiment execution of the instructions further cause the processor to render the magnetic resonance fingerprint chart on a display medium. A display medium as used herein may encompass an electronic or permanent method of display. For example the display medium may be a display on a screen or touchscreen display. A display medium may also include a printed or rendered image. For example the magnetic resonance fingerprint could be produced onto a standard transparency that is used by radiologists.

In another embodiment execution of the instructions further cause the processor to superimpose a representation of a subject onto the rendering of the magnetic resonance fingerprint chart. For example if the magnetic resonance fingerprint chart is simply a chart showing the concentrations of substances and function of position it may be difficult for a physician or other healthcare provider to interpret it. By placing an image or representation of a subject onto the chart it may enable easier interpretation by the user. For example a rendering of a person in the form of a line drawing, photograph, or even a magnetic resonance image may be useful.

In another embodiment execution of the instructions further causes the processor to align the representation of the subject in the rendering of the magnetic resonance fingerprint chart. This may be useful because then the representation of the subject is aligned with the fingerprint chart.

In another embodiment the representation of the subject is aligned with the magnetic resonance fingerprint chart using a predefined relationship between the representation and the location along the predetermined direction. For example the subject could be mounted in a subject support which has structures that force the subject's anatomy into a predetermined relationship with the subject support. The position of a subject support could then be registered to the location in the magnetic resonance imaging system.

In another embodiment the alignment of the representation with the magnetic resonance fingerprint chart is performed by matching the abundance of at least one of the predetermined substances with an anatomical location indicated by the representation of the subject. For instance certain parts of the subject's body or structure may have a large amount or lack particular substances. This could be used for aligning the fingerprint.

In another embodiment the magnetic resonance imaging system further comprises a subject support operable for stepwise moving of the subject through the imaging zone along the predetermined direction. Execution of the instructions further cause the processor to control the subject support to move the subject through the imaging zone along the predetermined direction during acquisition of the magnetic resonance data. The division of the magnetic resonance data into the slices is at least partially determined by the position of the subject support during the acquisition of the magnetic resonance data. In this embodiment the subject may be stepwise moved through the magnetic resonance imaging system so that a larger region of the subject along the predetermined direction is performed. For example a subject could have the complete structure or body imaged by moving the whole body or structure through the magnetic resonance imaging system.

In another embodiment the magnetic resonance imaging system further comprises a radio-frequency system for acquiring the magnetic resonance data. The radio-frequency system comprises a radio-frequency antenna for receiving magnetic resonance signals from a subject within the imaging zone. The radio-frequency antenna is a surface coil. A surface coil as used herein is a coil placed on the subject. The surface coil may have many separate elements for receiving or sending a local radio-frequency signal. The many separate elements or multiple separate elements may each be connected to its own radio-frequency channel. In this case the surface coil may be used for parallel imaging.

In another embodiment execution of the instructions further causes the processor to repeat measurement of the magnetic resonance data of at least one calibration phantom. Each of the at least one calibration phantoms has a calibration axis. The at least one calibration phantom comprises a known volume for each of the predetermined substances when the calibration axis is aligned with the predetermined direction. The use of a calibration phantom in this manner may be beneficial because it allows an absolute amount of a particular substance within a slice to be determined as opposed to relative amounts being determined.

In another embodiment the magnetic field gradient generator comprises a single gradient coil for generating the gradient magnetic field.

In another embodiment the magnetic field gradient generator comprises variations of windings within the main magnet to generate the gradient magnetic field. In this example the magnet has a permanent gradient magnetic field. This may be beneficial because a simple and inexpensive system for performing the one-dimensional magnetic resonance fingerprinting technique may be very inexpensive in comparison to a conventional magnetic resonance imaging system. There is no need for gradient coils or gradient coil amplifiers.

In another aspect the invention provides for a method of operating a magnetic resonance imaging system for acquiring the magnetic resonance fingerprint chart from a subject within an imaging zone. The magnetic resonance imaging system comprises a magnet for generating a main magnetic field within the imaging zone. The magnetic resonance imaging system further comprises a magnetic field gradient generator for generating a gradient magnetic field within the imaging zone. The gradient magnetic field is aligned with a predetermined direction. The magnetic resonance imaging system further comprises a memory for storing machine-executable instructions, a pre-calculated magnetic resonance fingerprint dictionary, and pulse sequence instructions. The pulse sequence instructions cause the magnetic resonance imaging system to acquire magnetic resonance data according to a magnetic resonance fingerprinting technique. The magnetic resonance fingerprinting technique encodes the magnetic resonance data as slices.

The pre-calculated magnetic resonance fingerprinting dictionary contains a listing of calculated magnetic resonance signals in response to execution of the pulse sequence instructions for a set of predetermined substances. The method comprises the step of acquiring the magnetic resonance data by controlling the magnetic resonance imaging system with the pulse sequence instructions. The method further comprises the step of dividing the magnetic resonance data into a set of slices. The method further comprises the step of calculating the abundance of each of the set of predetermined substances within each of the set of slices by comparing the magnetic resonance data for each of the set of slices with the pre-calculated magnetic resonance fingerprinting dictionary. The method further comprises the step of calculating the magnetic resonance fingerprinting chart by plotting the abundance of each of the predetermined substances within each of the set of slices as a function of position along the predetermined direction.

In another aspect the invention provides for a computer program product for execution by a processor controlling a magnetic resonance imaging system for acquiring a magnetic resonance fingerprint chart from a subject within an imaging zone. The magnetic resonance imaging system comprises a magnet for generating a main magnetic field within the imaging zone. The magnetic resonance imaging system further comprises a magnetic field gradient generator for generating a gradient magnetic field within the imaging zone. The gradient magnetic field is aligned with a predetermined direction.

The magnetic resonance imaging system further comprises a memory for storing machine-executable instructions, a pre-calculated magnetic resonance fingerprinting dictionary, and pulse sequence instructions. The pulse sequence instructions cause the magnetic resonance imaging system acquiring the magnetic resonance data according to a magnetic resonance fingerprinting technique. The magnetic resonance fingerprinting technique encodes the magnetic resonance data as slices. The pre-calculated magnetic resonance fingerprinting dictionary contains a listing of calculated magnetic resonance signals in response to execution of the pulse sequence instructions for a set of predetermined substances.

Execution of the machine-executable instructions causes the processor to acquire the magnetic resonance data by controlling the magnetic resonance imaging system with the pulse sequence instructions. Execution of the machine-executable instructions further causes the processor to divide the magnetic resonance data into a set of slices. Execution of the machine-executable instructions further cause the processor to calculate the abundance of each of the predetermined substances in each of the set of slices by comparing the magnetic resonance data for each of the set of slices with the pre-calculated magnetic resonance fingerprinting dictionary. Execution of the machine-executable instructions cause the processor to calculate the magnetic resonance fingerprint chart by applying abundances of each of the predetermined substances within each of the set of slices as a function of position along the predetermined direction.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
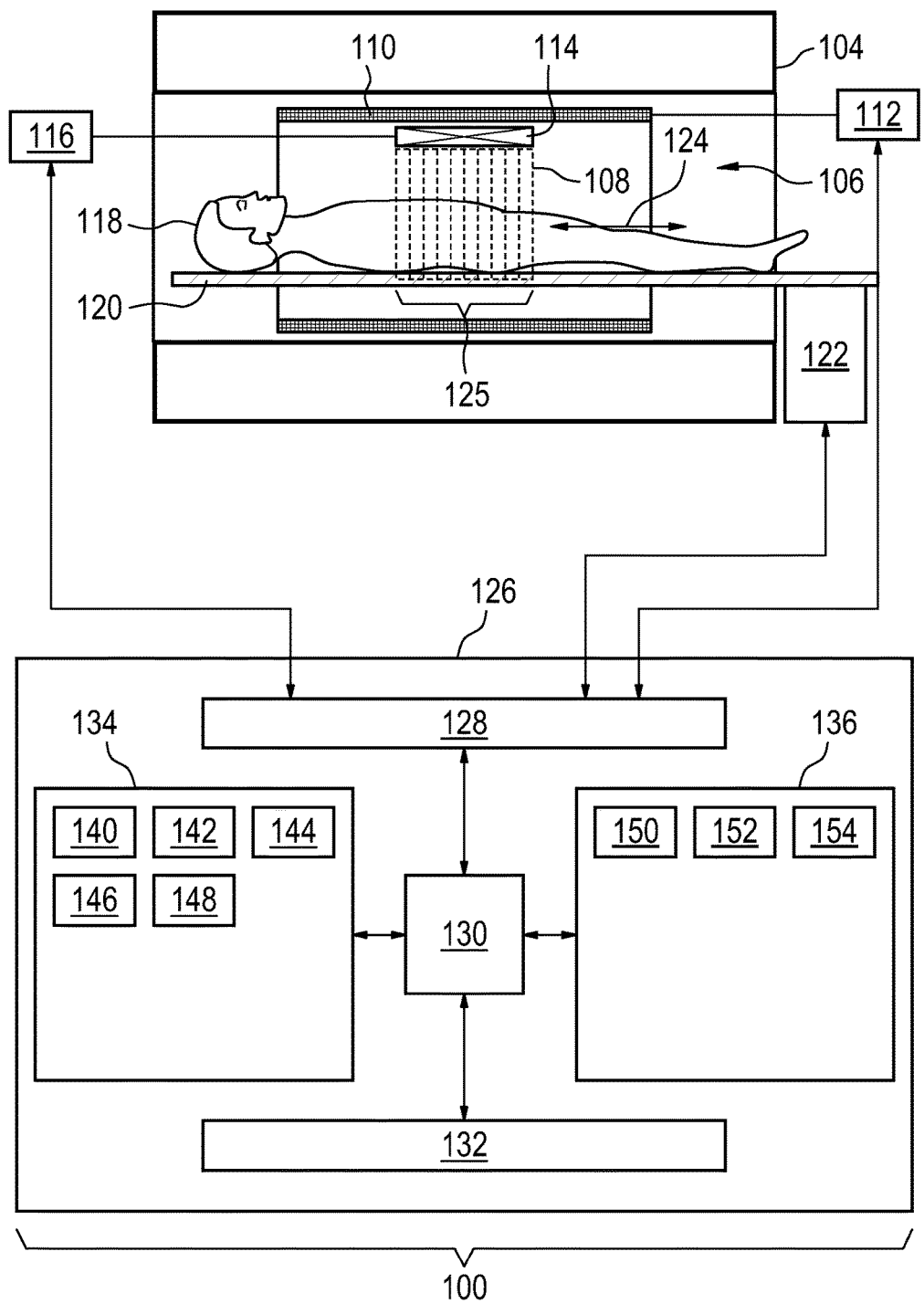
FIG. 1 illustrates an example of magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels.

The subject support 120 is attached to an optional actuator 122 that is able to move the subject support and the subject 118 through the imaging zone 108. In this way a larger portion of the subject 118 or the entire subject 118 can be imaged. The line with arrows labeled 124 is along the so-called z-axis of the magnet 104. The gradient field system 110, 112 may be used to make a gradient field in the direction along direction 124. The imaging zone 108 can be divided into a number of slices 125 that are perpendicular to the direction 124. The one-dimensional magnetic resonance fingerprinting technique can be applied along the direction 124 to determine the composition of the substances within each of the slices 125. The transceiver 116, the magnetic field gradient coil power supply 112 and the actuator 122 are all see as being connected to a hardware interface 128 of computer system 126.

The computer storage 134 is shown as containing pulse sequence instructions 140. The computer storage 134 is further shown as containing magnetic resonance data 142 that was acquired using the pulse sequence instructions 140 to control the magnetic resonance imaging system 100. The computer storage 134 is further shown as containing a magnetic resonance fingerprinting dictionary 144. The computer storage 134 is further shown as containing a magnetic resonance fingerprinting chart 146. The magnetic resonance fingerprinting chart 146 was reconstructed using the magnetic resonance data 142 and the magnetic resonance fingerprinting dictionary 144. The computer storage 134 further contains a rendering of the magnetic resonance fingerprint chart 148.

The computer memory 136 contains a control module 150 which contains such code as operating system or other instructions which enables the processor 130 to control the operation and function of the magnetic resonance imaging system 100. The computer memory 136 is further shown as containing a fingerprint chart generating module 152 which uses the magnetic resonance data 142 and the magnetic resonance fingerprinting dictionary 144 to calculate the magnetic resonance fingerprinting chart 146. The computer storage 136 further contains a rendering module 154 which is used for plotting and rendering the magnetic resonance fingerprinting chart 146 into the rendering of the magnetic resonance fingerprint chart 148. For instance the rendering of the magnetic resonance fingerprinting chart 148 could be rendered on the user interface 132 on a display.

Figure 2:
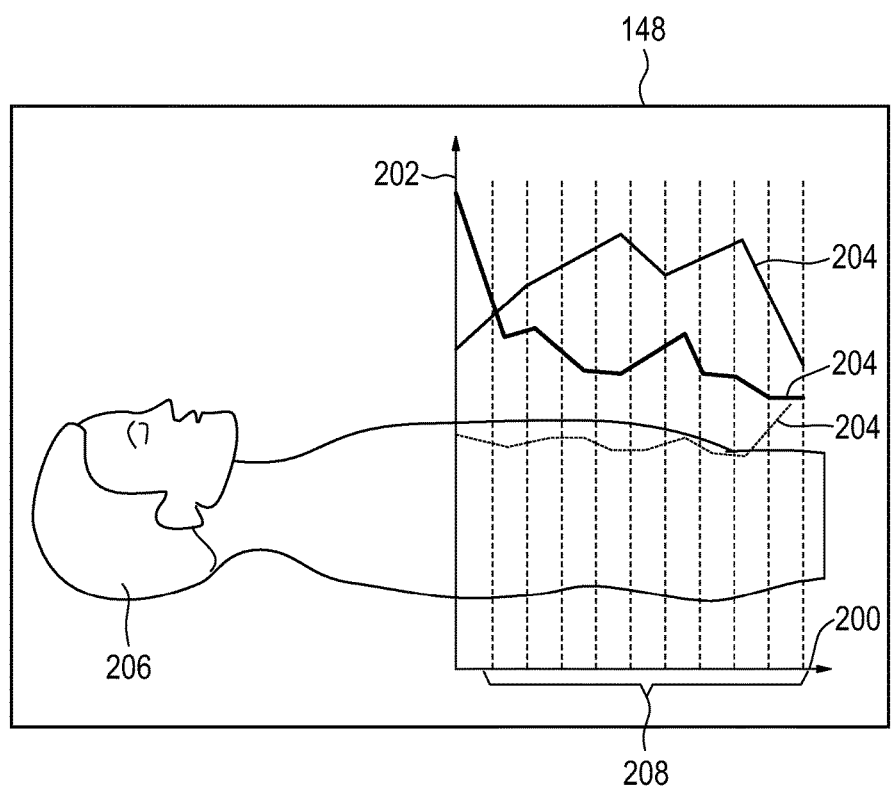
FIG. 2 illustrates a rendering of a magnetic resonance fingerprint chart.

FIG. 2 shows an exemplary rendering 148 of a magnetic resonance fingerprinting chart. In this example there is a chart with two axes 200, 202. Axis 200 is the distance along the direction 124. The y-axis 202 shows the concentration of a particular substance. Lines labeled 204 are the concentrations of different substances which were determined using the magnetic resonance fingerprinting dictionary 144. The profile 206 is a representation of the subject which is placed by the curves 204 so that the concentration relative to the anatomy of the subject can be inferred easily. The additional dashed lines 208 are there to help relate a particular concentration to an anatomical location within the representation of the subject 206.

Figure 3:
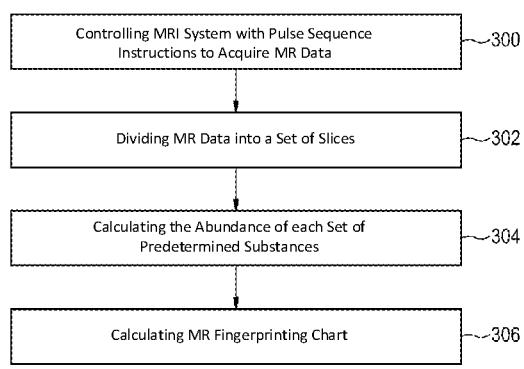
FIG. 3 illustrates a method of operating the magnetic resonance imaging system of claim 1.

FIG. 3 shows a flowchart, which illustrates a method of operating the magnetic resonance imaging system 100 of FIG. 1. First in step 300 the magnetic resonance data 142 is acquired by controlling the magnetic resonance imaging system 100 with the pulse sequence instructions 140. Next in step 302 the magnetic resonance data 142 is divided into a set of slices 125. Next in step 304 the abundance of each of the set of predetermined substances 204 calculated within each of the set of slices by comparing the magnetic resonance data for each of the set of slices with the pre-calculated magnetic resonance fingerprinting dictionary 144. Next in step 306 the magnetic resonance fingerprinting chart 146 is calculated by plotting 148 an abundance of each of the predetermined substances 204 within each of the set of slices as a function of position along the predetermined direction 124.

Magnetic Resonance (MR) fingerprinting is a new and very promising technique for the determination of tissue types by comparison of an MR measurement to a number of pre-calculated dictionary entries.

This invention builds upon the idea of MR fingerprinting in combination with an MR of scanner of reduced complexity and dedicated sequences and reconstruction algorithms to open up new opportunities for very efficient cancer screening or quantitative large-volume measurements.

Magnetic resonance fingerprinting has a high potential for accurate tissue characterization. Still, the current technique is based on a voxel-wise analysis of MR images and therefore is both time-consuming and expensive.

The present invention proposes a way to efficiently detect and quantify the existence of specific tissue types while:
1. Reducing hardware cost and energy consumption
2. Increasing patient throughput This may enable new applications for early cancer detection or for body fat quantification.

Examples may have one or more of the following features:
1. An MRI system with reduced hardware requirements: Low-performance x- and y-coils are possible; these coils may even be left out completely (a z-gradient coil can be designed to be very efficient).
2. A dedicated image acquisition sequence for B0-independent magnetic resonance fingerprinting
3. A dedicated reconstruction algorithm which determines relative and absolute volumes of different tissue types
4. A display device to visualize the findings Instead of producing and analysing medical images based on voxels, the method described here yields a tissue component analysis of a whole z-slice. A single dedicated fingerprint measurement (duration of a few seconds) is performed without employing in-plane (x, y) gradients. The tissue composition of the whole slice and the relative abundance of the tissue components are determined automatically from the resulting signal.

The MR sequence to be used preferably fulfills two requirements: First, it is sensitive to tissue-specific parameters (e.g. T1 and T2 values, others are conceivable, too) to encode the tissues of interest and allow quantitative tissue characterization by matching the measured signal against a dictionary (MR fingerprinting). Second, the signal is independent of non-tissue specific parameter variations (e.g. $B_0$ variations), so that matching the tissue components is possible over the whole slice.

Figure 4:
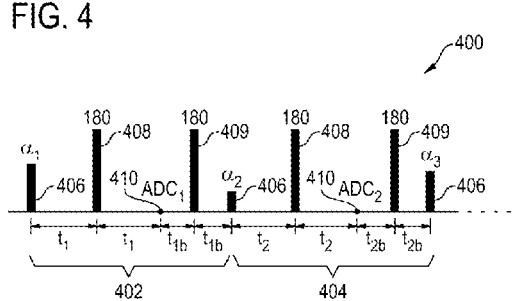
FIG. 4 illustrates an example of a pulse sequence.

FIG. 4 illustrates one example of such a sequence, which is sensitive to $T_1$ and $T_2$ but independent of $B_0$ variations. The sequence is based on a random or otherwise freely chosen list of flip angles $\alpha_i$ and delay times $t_i$. After the first RF pulse with flip angle $\alpha 1$, an echo is produced after a delay of $2t_1$ and the signal is recorded (ADC1). Another echo step with length $2t_{1b}$ ensures that the dephasing is again eliminated before the next part of the fingerprint sequence begins with flip angle $\alpha_2$ and delay $t_2$.

The additional echoes after the measurement points $ADC_i$ can be kept as short as possible with $t_{1b}=t_{2b}=\ldots$. A slice-selection gradient is switched on for each RF pulse using the z gradient coil.

FIG. 4 shows a portion of a pulse sequence 400. The pulse sequence may be used for generating or calculating the pulse sequence instructions 140. In this timing diagram a first pulse repetition 402 is shown and a second pulse repetition 404 is shown. Each pulse repetition begins with a radio-frequency pulse 406. The duration of the pulse repetition varies from pulse repetition to pulse repetition. There is a duration 410 where the radio-frequency signal is measured. The time between the radio-frequency pulse 406 and the measurement duration 410 is also varied as is the amplitude and/or shape of the particular radio-frequency pulses 406. This pulse sequence 400 also shows two 180° refocusing pulses 408, 409 per repetition 402, 404. The first refocusing pulse 408 is located at the temporal midpoint between the radio-frequency pulse 406 and the measurement duration 410. The second radio-frequency pulse 409 is located between the midpoint of the measurement duration 410 and the start of the next pulse 406. The first refocusing pulse 408 causes the radio-frequency signal to be refocused when the measurement 410 is made. The second refocusing pulse 409 causes the signal to be refocused when the next pulse 404 starts.

The effect of using the two refocusing pulses 408 and 409 is that the effect of any inhomogeneities in the magnetic field is reduced or minimized. This may reduce the signal-to-noise in the end magnetic resonance fingerprinting chart and it also makes it easier to make the pre-calculated magnetic resonance fingerprinting dictionary. Without this compensation it may be necessary to include effects of the inhomogeneities in the calculations used to make the pre-calculated magnetic resonance fingerprinting dictionary.

The measured MR signal (a list of all the $ADC_i$ values) is compared with the pre-calculated dictionary for all combinations of $T_1$ and $T_2$ to be expected in the volume. The dictionary is created by solving the Bloch equations for the fingerprinting sequence described above for different combinations of $T_1$ and $T_2$.

In order to determine the tissue composition of the whole slice, the signal is expressed as a (complex) linear combination of the N dictionary entries, $$s=\Sigma_{k=0}^{N} a_k d_k$$

where s is the signal vector and $d_k$ are the dictionary entries. The coefficients $a_k \geq 0$ are determined by the reconstruction algorithm. This is accomplished by solving the least squares problem $$\text{minimize } \|Da-s\|_2$$

$$\text{for } a_k \geq 0$$

where D is the dictionary matrix with dictionary entries $d_k$ as columns and a is the vector of coefficients describing the contribution of the individual potential tissues components/tissue types to the detected signal.

Each dictionary entry is assigned to a certain tissue type. Thus, the coefficients $a_k$ yield an estimate for the relative abundance of the different tissue components in terms of the "number of spins" involved for each component.

In a further step, these relative "spin numbers" can be converted estimates of relative volumes or relative masses of the tissue components if the spin density of the different tissue types is known.

The system does not produce spatially resolved images. The only spatial resolution is achieved in the z-direction (or other single direction) by applying the RF pulses shown in FIG. 4 in a slice selective manner. However, for each slice, the composition of tissue types is determined and can be visualized as numbers, bar graphs, etc. In the case of a multi-slice scan, the abundance of the different components can be displayed as a function of the z position.

The system may be programmed in such a way that it alerts the operator if certain types of tissue are found (e.g., suspicious masses, potential tumors). It can also be programmed in such a way that it displays the total volume/relative abundance of specified tissues, e.g. metastases of a certain kind or fat fraction.

In one example, the MRI system contains no x or y gradient coils. Only a z gradient coil is provided.

In one example, the MRI system contains no gradient coil at all. A static z gradient is provided by a dedicated MR magnet with asymmetric windings.

In one example, a slightly higher spatial resolution, preferable in-plane, could be achieved by using spatially sensitive local reception coils, which are placed closed to the body surface.

In one example, a number of measurements are performed, while the patient table is moved stepwise automatically. In this way, a large part of the body or the whole body can be scanned.

In another example, using moving table technology, the patient is moved through a sensitive receive array ("carwash approach") to improve spatial resolution and SNR and to reduce costs of too many receivers.

In one example, a gauge measurement using a known volume of a known substance is performed once to determine the factor of proportionality linking the volume/mass of the substance to the value of the relative volume/mass determined by measurement. In this way, all subsequently measured relative volumes/masses can be converted to absolute tissue volumes/masses.

Figure 5:
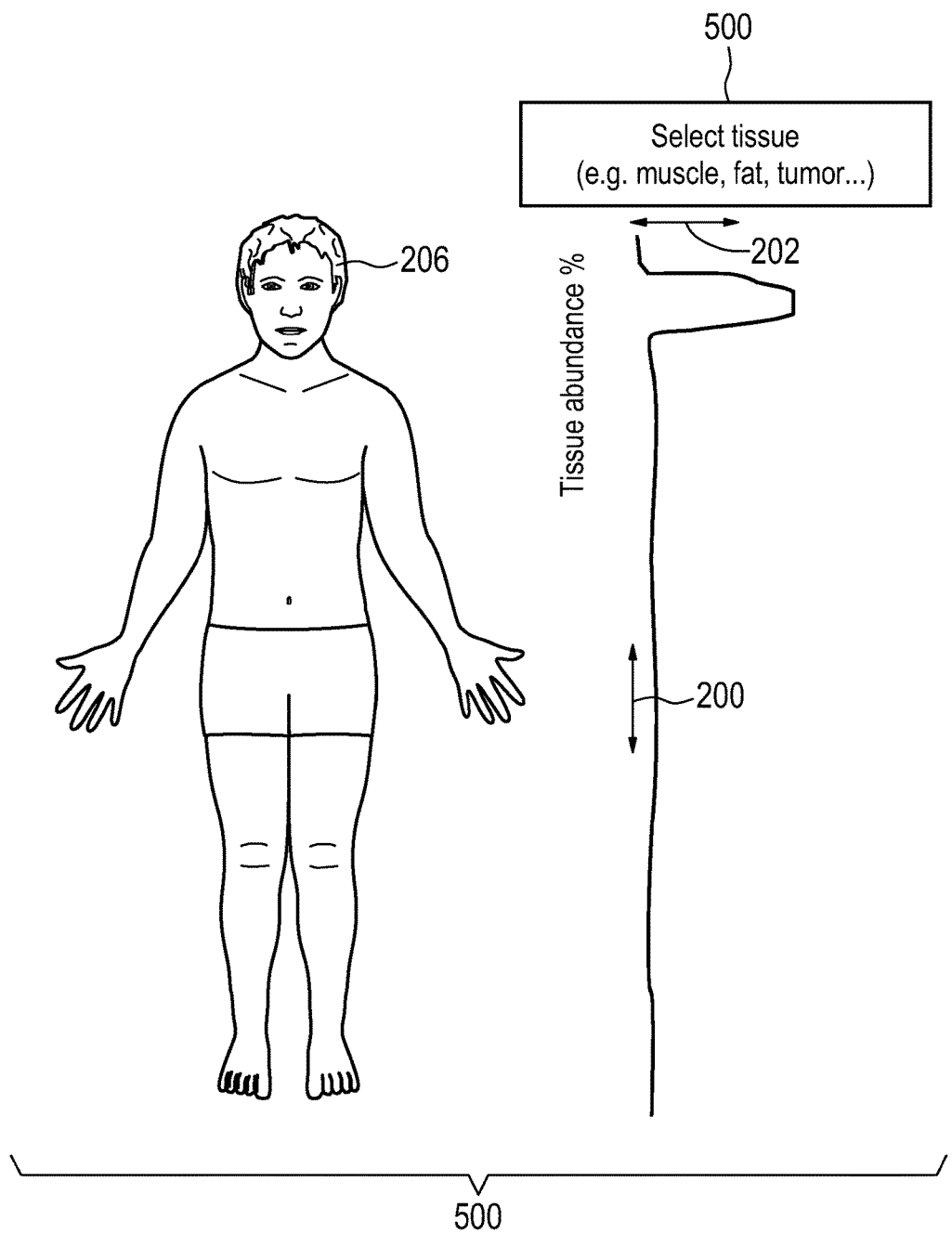
FIG. 5 illustrate a further example of a rendering of a magnetic resonance fingerprint chart.

FIG. 5 shows a further exemplary rendering 500 of a magnetic resonance fingerprinting chart. In this example there is a chart with two axes 200, 202. Axis 200 is the distance along the direction 124. The axis 202 shows the concentration of a particular substance. In this example the concentration is expressed as a curve 204 which plots the percent abundance of a selected tissue type as a function of distance along the axis 200. A profile 206 is a representation of the subject which is placed by the curve 204 so that the concentration relative to the anatomy of the subject can be inferred easily. In case the magnetic fingerprint chart is rendered on a user interface or a graphical user interface there may also be additional control objects 500 which allows a user to modify or change the rendering. The control object 500 could for example be used to select which substance or tissue is displayed. The control object could also allow multiple tissue types to be displayed simultaneously. The control object could also be used to modify the scale, zoom region, and/or scale type. For example the scale could be changed between being a relative abundance of multiple tissue types, a the percentage of a tissue or substance abundance, the concentration, or in terms of the absolute mass distributed along the direction 124.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 magnetic resonance imaging system
104 magnet
106 bore of magnet
108 imaging zone
110 magnetic field gradient coils
112 magnetic field gradient coil power supply
114 radio-frequency coil
116 transceiver
118 subject
120 subject support
122 actuator
124 predetermined direction
125 slices
126 computer system
128 hardware interface
130 processor
132 user interface
134 computer storage
136 computer memory
140 pulse sequence instructions
142 magnetic resonance data
144 magnetic resonance fingerprinting dictionary
146 magnetic resonance finger print chart
148 rendering of magnetic resonance fingerprint chart
150 control module
152 fingerprint chart generation module
154 rendering module
200 distance along direction 124
202 axis indicating concentration of substance
204 plot of concentration of a substance
206 representation of subject
208 dashed lines to help reference concentrations to anatomy
300 acquire the magnetic resonance data by controlling the magnetic resonance imaging system with pulse sequence instructions
302 divide the magnetic resonance data into a set of slices
304 calculate the abundance of each of the predetermined substances within each of the set of slices by comparing the magnetic resonance data for each of the set of slices with the pre-calculated magnetic resonance fingerprinting dictionary
306 calculate the magnetic resonance fingerprint chart by plotting the abundance of each of the predetermined substances within each of the set of slices as a function of position along the predetermined direction
400 pulse sequence
402 first pulse repetition
404 second pulse repetition
406 RF pulse
408 first 180 degree refocusing pulse
409 second 180 degree refocusing pulse
410 measurement or radio frequency signal

The invention claimed is:

1. A magnetic resonance imaging system for acquiring a magnetic resonance data from a subject within an imaging zone, wherein the magnetic resonance imaging system comprises:

a magnet for generating a main magnetic field within the imaging zone;

a magnetic field gradient generator for generating a gradient magnetic field within the imaging zone, wherein the gradient magnetic field is aligned with a predetermined direction;

a non-transitory computer readable memory for storing machine executable instructions, a pre-calculated magnetic resonance fingerprinting dictionary, and pulse sequence instructions, wherein the pulse sequence instructions cause the magnetic resonance imaging system to acquire the magnetic resonance data according to a magnetic resonance fingerprinting technique, wherein the magnetic resonance fingerprinting technique encodes the magnetic resonance data as slices, wherein the pre-calculated magnetic resonance fingerprinting dictionary contains a listing of calculated magnetic resonance signals in response to execution of the pulse sequence instructions for a set of predetermined substances;

a processor for controlling the magnetic resonance imaging system, wherein execution of the machine executable instructions causes the processor to:

acquire the magnetic resonance data by controlling the magnetic resonance imaging system with pulse sequence instructions;

divide the magnetic resonance data into a set of slices;

calculate the abundance of each of the set of predetermined substances within each of the set of slices by comparing the magnetic resonance data for each of the set of slices with the pre-calculated magnetic resonance fingerprinting dictionary; and calculate a magnetic resonance fingerprint chart by plotting abundance of each of the set of predetermined substances within each of the set of slices as a function of position along the predetermined direction.

2. The magnetic resonance imaging system of claim 1, wherein the pulse sequence comprises a train of pulse repetitions, wherein each pulse repetition of the train of pulse repetitions has a random duration, a preselected duration from distribution of durations, or a pseudorandom duration, wherein each pulse repetition comprises a radio frequency pulse chosen from a distribution of flip angles to rotate magnetic spins, and wherein each pulse repetition comprises a sampling event where the magnetic resonance signal is sampled for a predetermined duration at a predetermined time before the end of the repetition pulse, wherein the magnetic resonance data is acquired during the sampling event.

3. The magnetic resonance imaging system of claim 2, wherein each pulse repetition of the pulse sequence comprises a first 180 degree RF pulse performed at a first temporal midpoint between the radio frequency pulse and the sampling event to refocus the magnetic resonance signal, and wherein each pulse repetition of the pulse sequence comprises a second 180 degree RF pulse performed at a second temporal midpoint between the sampling event and the start of the next pulse repetition in order to reduce the dependency of the signal on inhomogeneities in the main magnetic field within the imaging zone.

4. The magnetic resonance imaging system of claim 1, wherein the calculation of the abundance of each of the predetermined tissue types within each of the set of slices by comparing the magnetic resonance data for each of the set of slices with the pre-calculated magnetic resonance fingerprinting dictionary is performed by:

expressing each magnetic resonance signal of the magnetic resonance data as a linear combination of the signal from each of the set of predetermined substances, and determining the abundance of each of the set of predetermined substances by solving the linear combination using a minimization technique.

5. The magnetic resonance imaging system of claim 1, wherein execution of the instructions further causes the processor to render the magnetic resonance fingerprint chart on a display medium.

6. The magnetic resonance imaging system of claim 5, wherein execution of the instructions further causes the processor to superimpose a representation of a subject onto the rendering of the magnetic resonance fingerprint chart.

7. The magnetic resonance imaging system of claim 6, wherein execution of the instructions further causes the processor to align the representation of the subject in the rendering of the magnetic resonance fingerprint chart using any one of the following: use a pre-defined relationship between the representation and a location along the predetermined direction, and match the abundance of at least one of the set of predetermined substances with an anatomical location indicated by the representation of the subject.

8. The magnetic resonance imaging system of claim 1, wherein the magnetic resonance imaging system further comprises a subject support operable for stepwise moving of the subject through the imaging zone along the predetermined direction, wherein execution of the instructions further causes the processor to:

control the subject support to move the subject through the imaging zone along the predetermined direction during acquisition of the magnetic resonance data, wherein the division of the magnetic resonance data into the set of slices is at least partially determined by the position of the subject support during the acquisition of the magnetic resonance data.

9. The magnetic resonance imaging system of claim 8, wherein the magnetic resonance imaging system further comprises a radio frequency system for acquiring the magnetic resonance data, wherein the radio frequency system comprises a radio frequency antenna for receiving magnetic resonance signals from the subject within the imaging zone, wherein the radio frequency antenna is a surface coil.

10. The magnetic resonance imaging system of claim 1, wherein execution of the instructions further causes the processor to repeat measurement of the magnetic resonance data of at least one calibration phantom, wherein each of the at least one calibration phantom has a calibration axis, wherein the at least one calibration phantom comprises a known volume of at least one of the set of predetermined substances when the calibration axis is aligned with the predetermined direction.

11. The magnetic resonance imaging system of claim 1, wherein the magnetic field gradient generator comprises a single gradient coil for generating the gradient magnetic field.

12. The magnetic resonance imaging system of claim 1, wherein the magnetic field gradient generator comprises variations of winding within the main magnet to generate the gradient magnetic field.

13. A method of operating a magnetic resonance imaging system for acquiring magnetic resonance data from a subject within an imaging zone, wherein the magnetic resonance imaging system comprises:

a magnet for generating a main magnetic field within the imaging zone;

a magnetic field gradient generator for generating a gradient magnetic field within the imaging zone, wherein the gradient magnetic field is aligned with a predetermined direction; and a memory for storing machine executable instructions, a pre-calculated magnetic resonance fingerprinting dictionary, and pulse sequence instructions, wherein the pulse sequence instructions cause the magnetic resonance imaging system to acquire the magnetic resonance data according to a magnetic resonance fingerprinting technique, wherein the magnetic resonance fingerprinting technique encodes the magnetic resonance data as slices, wherein the pre-calculated magnetic resonance fingerprinting dictionary contains a listing of calculated magnetic resonance in response to execution of the pulse sequence instructions for a set of predetermined substances;

wherein the method comprises the steps of:

acquiring the magnetic resonance data by controlling the magnetic resonance imaging system with the pulse sequence instructions;

dividing the magnetic resonance data into a set of slices;

calculating the abundance of each of the set of predetermined substances within each of the set of slices by comparing the magnetic resonance data for each of the set of slices with the pre-calculated magnetic resonance fingerprinting dictionary; and calculating a magnetic resonance fingerprint chart by plotting abundance of each of the set of predetermined substances within each of the set of slices as a function of position along the predetermined direction.

14. A computer program product for execution by a processor controlling a magnetic resonance imaging system for acquiring magnetic resonance data from a subject within an imaging zone, wherein the magnetic resonance imaging system comprises:

a magnet (104) for generating a main magnetic field within the imaging zone;

a magnetic field gradient generator for generating a gradient magnetic field within the imaging zone, wherein the gradient magnetic field is aligned with a predetermined direction; and a memory for storing a pre-calculated magnetic resonance fingerprinting dictionary, and pulse sequence instructions, wherein the pulse sequence instructions cause the magnetic resonance imaging system to acquire the magnetic resonance data according to a magnetic resonance fingerprinting technique, wherein the magnetic resonance fingerprinting technique encodes the magnetic resonance data as slices, wherein the pre-calculated magnetic resonance fingerprinting dictionary contains a listing of calculated magnetic resonance signals in response to execution of the pulse sequence instructions for a set of predetermined substances;

wherein execution of the machine executable instructions causes the processor to:

acquire the magnetic resonance data by controlling the magnetic resonance imaging system with the pulse sequence instructions;

divide the magnetic resonance data into a set of slices;

calculate the abundance of each of the set of predetermined substances within each of the set of slices by comparing the magnetic resonance data for each of the set of slices with the pre-calculated magnetic resonance fingerprinting dictionary; and calculate the magnetic resonance fingerprint chart by plotting abundance of each of the set of predetermined substances within each of the set of slices as a function of position along the predetermined direction.

* * * * *